United States Patent [19]

Saxton et al.

[11] Patent Number: 5,695,736
[45] Date of Patent: Dec. 9, 1997

[54] TIATANIUM CONTAINING MOLECULAR SIEVE HAVING A ZELITE BETA STRUCTURE

[75] Inventors: Robert J. Saxton, West Chester; John G. Zajacek, Devon, both of Pa.; Guy L. Crocco, Wilmington, Del.

[73] Assignee: ARCO Chemical Technology, L.P., Greenville, Del.

[21] Appl. No.: 769,472

[22] Filed: Dec. 20, 1996

Related U.S. Application Data

[63] Continuation of Ser. No. 622,799, Mar. 27, 1996, abandoned, which is a continuation of Ser. No. 302,554, Sep. 8, 1994, abandoned, which is a division of Ser. No. 172,405, Dec. 23, 1993, Pat. No. 5,374,747.

[51] Int. Cl.$^6$ .............................. C01B 39/06; B01J 29/04
[52] U.S. Cl. .................. 423/700; 423/713; 423/714; 423/DIG. 27; 502/85; 502/86
[58] Field of Search .................. 423/700, 713, 423/714, DIG. 27; 502/85, 86

[56] References Cited

U.S. PATENT DOCUMENTS

| | | | |
|---|---|---|---|
| 4,410,501 | 10/1983 | Taramasso et al. | |
| 4,576,805 | 3/1986 | Chang et al. | |
| 4,666,692 | 5/1981 | Taramasso et al. | |
| 4,824,976 | 4/1989 | Clehce et al. | 549/531 |
| 4,827,068 | 5/1989 | Chen et al. | 585/408 |
| 4,828,812 | 5/1989 | McCullen e tal. | |
| 4,833,260 | 5/1989 | Neri et al. | 549/531 |
| 4,892,720 | 1/1990 | Skuls et al. | 423/308 |
| 5,098,687 | 3/1992 | Skeels et al. | |
| 5,214,168 | 5/1993 | Zahaur et al. | 549/531 |
| 5,246,690 | 9/1993 | Bellussi et al. | 423/705 |
| 5,262,550 | 11/1993 | Crocco et al. | 549/531 |
| 5,310,534 | 5/1994 | Fajula et al. | 423/715 |
| 5,527,520 | 6/1996 | Saxton et al. | 423/DIG. 27 |

FOREIGN PATENT DOCUMENTS

| | | |
|---|---|---|
| 077522 | 10/1982 | European Pat. Off. |
| 2694549 | 8/1992 | France. |
| 2037596 | 7/1991 | Spain. |
| WO8504856 | 7/1985 | WIPO. |
| WO9402245 | 2/1994 | WIPO. |

OTHER PUBLICATIONS

Kim et al., Catalysis Letters 22 pp. 259-270 (1993) No Month.

Catalysis Letters 1, B. Krayshaar et al. pp. 81-84 (1988) No Month.

Krayshaar-Czarnetzki et al., Catalysis Letter 2, 43-48 (1989) No Month.

Journal of Catalysis, A. Corma et al. pp. 151-158 (1994) No Month.

Catalysis Letters I. B. Kraushaar et al. pp. 85-92 (1988) No Month.

Heterogenrous Catalysis, R. Schlög, pp. 381-393 (1993) No Month.

Chemical Communications 8, M.A. Cambor et al., pp. 589-590 (1992) No Month.

Journal of Catlysis 130, A. Thangaraj et al., pp. 1-8 (1991) No Month.

"Single Step Dealumination etc.", . Lami et al., pp. 237-244 (1993) No Month.

Symposium Chemically Modified Molecular Sieves, Div. Pet. Chem. 206th Annual Meeting ACS, "Synthesis and Physicochemical etc." C.B. Dartt et al., pp. 491-493 (1993) No Month.

"Synthesis & Catalytic Properties of Titanium-Substituted Silicoaluminophosphet TAPSO-5" *J. Chem. Soc., Chem commun.*, 1994, Tuel et al. pp. 1667-1668 No Month.

Primary Examiner—Mark L. Bell
Assistant Examiner—Louis M. Troilo
Attorney, Agent, or Firm—Stephen D. Harper

[57] ABSTRACT

A crystalline molecular sieve having a framework structure isomorphous with zeolite beta and containing Si and Ti, but essentially no framework Al, usefully catalyzes olefin epoxidation wherein hydrogen peroxide is the oxidant.

6 Claims, 1 Drawing Sheet

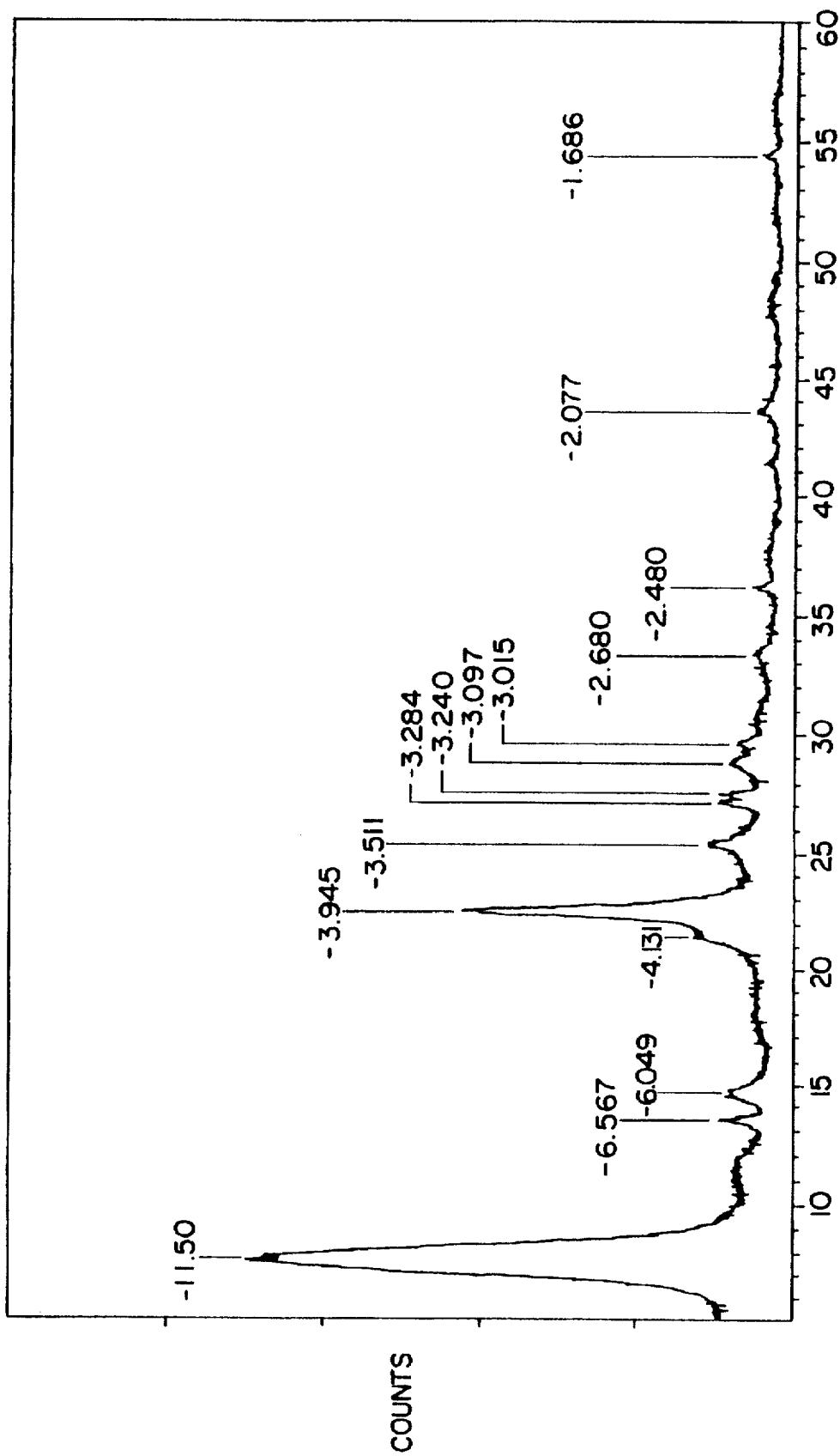

TIATANIUM CONTAINING MOLECULAR SIEVE HAVING A ZELITE BETA STRUCTURE

This is a continuation of application Ser. No. 08/622,799, filed Mar. 27, 1996, abandoned, which is a continuation of application Ser. No. 08/302,554, filed Sep. 8, 1994, abandoned, which is a division of application Ser. No. 08/172,405 filed, Dec. 23, 1993, now U.S. Pat. No. 5,374,747.

FIELD OF THE INVENTION

This invention relates to methods of selectively oxidizing olefins so as to obtain products containing epoxide functional groups. In particular, the invention pertains to processes whereby a hydrogen peroxide source is reacted with an ethylenically unsaturated substrate in the presence of a relatively large pore crystalline titanium-containing molecular sieve catalyst to yield an epoxide. The catalyst is characterized by a framework structure isomorphous to zeolite beta comprised of silica and titanium, but essentially free of framework aluminum.

BACKGROUND OF THE INVENTION

Many different methods for the preparation of epoxides have been developed. One such method involves the epoxidation of an olefin in a liquid phase reaction using an organic hydroperoxide as the oxidizing agent and certain solubilized transition metal compounds as catalyst. Although this approach is practiced commercially and generally provides high selectivity to epoxide, it has at least two characteristics which tend to limit process flexibility and increase production costs. The use of an organic hydroperoxide results in the generation of a co-product alcohol derived from the reacted hydroperoxide during epoxidation; approximately 1 equivalent of the co-product is obtained for each equivalent of epoxide. If no market exists for the alcohol, the co-product must either be further reacted (incurring additional processing costs) so as to convert it back to the hydroperoxide oxidant or to another compound for which a commercial demand exists. Recovery of the soluble metallic catalyst used in such a process for reuse in subsequent runs is also problematic. It would therefore be highly desirable to develop an insoluble (heterogeneous) epoxidation catalyst which has high activity and selectivity when utilized with an oxidant such as hydrogen peroxide which does not form an organic co-product. Such a catalyst would ideally be readily recoverable in active form from an epoxidation reaction mixture by filtration or similar separation techniques or be capable of being utilized in the form of a fixed bed or the like.

Workers at the Universidad Politecnica de Valencia have recently reported the synthesis of a titanium silicoaluminate isomorphous to zeolite beta (see Camblor et al., *J. Chem. Soc., Chem. Commun.* pp. 589–590 (1992), Camblor et al., *Zeolites* 13, pp. 82–87 (1993) and ES 2037596 (published Jun. 16, 1993)). Such aluminum-containing materials were found to catalyze the oxidation of alkanes to alcohols, ketones, and the like using hydrogen peroxide as the oxidant. This type of titanium silicoaluminate in unmodified (fully protonated) form is a poor catalyst for the production of epoxides from olefins, however.

SUMMARY OF THE INVENTION

We have now made the unexpected discovery that a crystalline titanium-containing molecular sieve characterized by a framework structure isomorphous to zeolite beta and comprised of Si and Ti atoms, but essentially free of framework aluminum, selectively catalyzes the epoxidation of olefins using hydrogen peroxide or a hydrogen peroxide precursor.

BRIEF DESCRIPTION OF THE DRAWING

FIG. 1 is an X-ray powder diffraction pattern of the titanium-containing molecular sieve prepared using the procedure of Example 1.

DETAILED DESCRIPTION OF THE INVENTION

In the process of this invention, an olefin is contacted with hydrogen peroxide or a substance capable of producing hydrogen peroxide under the reaction conditions in the presence of a catalytically effective amount of a titanium-containing molecular sieve. The titanium-containing molecular sieve suitable for use is characterized by a framework structure isomorphous to zeolite beta. Si and Ti atoms are present in the framework structure (typically, in the form of oxides). The framework of the molecular sieve is essentially free of aluminum (Al), however, since the presence of significant amounts of Al has been found to detrimentally affect the performance of said molecular sieve as an epoxidation catalyst unless the protons associated with aluminum are substituted with ammonium, alkali metal, or alkaline earth cations. In this context, "essentially free" means that the framework structure of the molecular sieve contains less than 1000 ppm Al. Preferably, less than 500 ppm Al is present in the framework structure. The Si to Al molar ratio (Si:Al) is advantageously at least 750, more preferably at least 1000. Most preferably, less than 100 ppm Al is present.

Zeolite beta is characterized by 12-member ring pore openings and a three dimensional interconnecting channel system; its framework structure is more completely described in U.S. Pat. No. 3,308,069, Szostak, *Handbook of Molecular Sieves*, pp. 92–96, Higgin et al., *Zeolites*, 8,446 (1986), and Treacy et al., *Nature*, 332, 249 (1988). The catalyst utilized in the invention thus has a fundamentally different structure than the titanium-containing molecular sieves reported in the prior art (e.g., the TS-1 catalyst described in U.S. Pat. No. 4,410,501, which has an MFI structure; the TS-2 catalyst described by Reddy et al. in *Appl. Cat.* 58, L1 (1990), which has a ZSM-11 structure).

In preferred embodiments, the titanium-containing molecular sieve has relatively large pores (equal to or greater than about 6 angstroms on average) and has a zeolite-type structure comprised of Si and a lesser amount of Ti. A crystallinity of greater than 75% is usually desirable. Preferably, the molar ratio of Ti: Si is from 0.1:99.9 to 20:80, with ratios in the range of 1:99 to 15:85 being especially preferred. The titanium-containing molecular sieve advantageously may have a titanium content of from 1 to 10 weight percent.

The general formula for the titanium-containing molecular sieve is preferably as follows:

$SiO_2:yTiO_2$ wherein y is from 0.01 to 0.25 (preferably, 0.03 to 0.20).

A suitable method for the preparation of the aforedescribed titanium-containing molecular sieves involves a procedure wherein zeolite beta is dealuminated and the framework vacancies created by dealumination filled by titanium atoms. This method is preferred for use since it is relatively rapid and provides high yields of active catalyst, as compared to, for example, hydrothermal techniques which can require 1 week or more per batch and which provide lower yields of catalyst. Post-synthesis dealumination methods are well-known and include, for example, reaction or leaching with mineral acids (e.g., HCl, $H_2SO_4$, $HNO_3$) or chelating agents and hydrothermal or steaming treatments (possibly combined with acid leaching). See, for example, the extensive listing of publications describing zeolite dealumination methods catalogued in U.S. Pat. No. 4,576,805 (col. 8, line 62 through col. 9, line 27) and Scherzer, "The Preparation and Characterization of Aluminum-Deficient Zeolites", ACS Syrup. Ser. 248, 157–200 (1984). A particularly preferred method employs treatment of zeolite beta with a mineral acid such as nitric acid (preferably, 2 to 13M; most preferably, concentrated nitric acid) at a temperature of from 25° C. to 150° C. for a period of time of from 5 minutes to 24 hours. Other mineral acids and carboxylic acids could alternatively be used, as described, for example, in British Pat. No. 1,061,847, European Pat. Publication No. 488,867, Kraushaar et al., Catalysis Letters 1, 81–84 (1988), Chinese Pat. No. 1,059,701 (Chem. Abst. 117:114655g), European Pat. Publication No. 95,304, and Chinese Pat. No. 1,048,835 (Chem. Abst. 115: 52861u). The beta zeolite is desirably suspended in or otherwise contacted with a relatively large volume of the nitric acid (preferably, from 10 to 1000 parts by weight nitric acid per 1 part by weight of the zeolite beta). Multiple dealuminations of this sort may be performed to effect more complete Al removal. Suitable dealumination methods of this type are described in more detail in Lami et al., Microporous Materials 1,237–245 (1993), and European Pat. Publication No. 488,867. The dealuminated material may thereafter be contacted with a titanium source. For example, the dealuminated zeolite beta may be exposed to a volatile titanium source such as $TiCl_4$, vapor in nitrogen for 1 to 24 hours at an elevated temperature (preferably, 250° C. to 750° C.). A liquid phase source of titanium such as $(NH_4)_2TiF_6$(aq.) or $TiF_4$(aq.) may alternately be utilized to insert Ti atoms into the framework vacancies of the dealuminated zeolite beta. Methods of post-synthesis titanium incorporation into zeolite materials are described, for example, in U.S. Pat. No. 4,576,805, U.S. Pat. No. 4,828,812, and Kraushaar, et al., Catal. Lett. 1, 81–84 (1988). It may be desirable to then treat the titanium-containing molecular sieve with an ammonium salt such as ammonium nitrate, an acid solution (such as aqueous nitric acid) or the like to convert the titanium source to acid form (i.e., hydrogen or hydronium form) or to remove extra-framework aluminum. Water-washing, drying, and/or calcination may also be advantageous.

To further enhance the performance of certain titanium-containing molecular sieves prepared as described hereinabove, it may be advantageous to contact the catalyst with an ammonium, alkali metal and/or alkaline earth metal compound. Without wishing to be bound by theory, it is believed that this enhancement is attributable to the neutralization of certain metal-associated acidic sites present in the titanium-containing molecular sieve. A preferred method for accomplishing this modification is to dissolve the ammonium, alkali metal or alkaline earth metal compound in water or other suitable liquid medium; the resulting solution is then brought into intimate contact with the molecular sieve. This procedure preferably is performed at a temperature sufficiently high so as to accomplish the partial (i.e., at least 25%) or complete exchange or replacement of the ammonium, alkali metal or alkaline earth metal for the hydrogen cations of the acidic sites within a practicably short period of time (e.g., within 24 hours). For this purpose, temperatures of from about 25° C. to 150° C. will generally suffice. The concentration of ammonium, alkali metal or alkaline earth metal compound in the liquid medium may be varied as desired and will typically be from about 0.001 to 5 molar. Optimum concentrations may be readily ascertained by routine experimentation. Following the desired cation exchange, the excess liquid medium may be separated from the modified titanium-containing molecular sieve by filtration, decantation, centrifugation, or other such technique, and the modified titanium-containing molecular sieve washed (if desired) with water or other liquid substance, and then dried and/or calcined prior to use in the epoxidation process of this invention. If an ammonium compound has been utilized, calcination is preferably avoided so as to minimize any re-protonation of the catalyst.

The particular ammonium, alkali metal or alkaline earth metal compound selected for use is not critical but preferably is water-soluble and is desirably selected from ammonium, alkali metal or alkaline earth metal hydroxides and oxides (e.g., sodium hydroxide, potassium hydroxide, barium hydroxide, calcium hydroxide), ammonium, alkali metal or alkaline earth metal carbonates (e.g., sodium carbonate, potassium carbonate), ammonium, alkali metal or alkaline earth metal bicarbonates (e.g., sodium bicarbonate, potassium bicarbonate), ammonium, alkali metal or alkaline earth metal nitrates (e.g., sodium nitrate, potassium nitrate), ammonium, alkali metal or alkaline earth metal halides (e.g., potassium chloride, sodium bromide, sodium chloride), ammonium, alkali metal or alkaline earth metal sulfates (e.g., sodium sulfate, potassium sulfate), ammonium, alkali metal or alkaline earth metal salts of carboxylic acids (e.g., sodium acetate), and the like and mixtures thereof. The counter anion in the ammonium, alkali metal or alkaline earth compound should be chosen such that it does not interfere with the desired epoxidation activity of the modified titanium-containing molecular sieve nor detrimentally alter its crystalline structure. For example, it has been found that under certain conditions the use of alkali metal pyrophosphates may deactivate or poison the molecular sieve catalyst.

In one embodiment of the invention, an ammonium, alkali metal, or alkaline earth-modified titanium-containing molecular sieve is generated in-situ during epoxidation through the use of an unmodified titanium-containing molecular sieve in combination with either an ammonium, alkali metal or alkaline earth compound of the type described previously or a buffer comprised of an ammonium, alkali metal or alkaline earth salt of a carboxylic acid or the like. For example, the reaction medium wherein the olefin is contacted with hydrogen peroxide may contain a NaOAc/HOAc buffer system (preferably, 0.1 to 5M) in a suitable solvent such as an alcohol (e.g., methanol). Alternatively, an alkali metal compound alone such as sodium acetate could be utilized. In a batch process, the ammonium, alkali metal or alkaline earth compound could, for example, be added by itself prior to initiation of epoxidation while in a continuous process (as when a CSTR reactor is employed) such compound could be combined with one of the feed streams containing one of the other reaction components such as the hydrogen peroxide.

The amount of catalyst employed is not critical, but should be sufficient so as to substantially accomplish the desired epoxidation reaction in a practicably short period of time. The optimum quantity of catalyst will depend upon a number of factors including reaction temperature, olefin reactivity and concentration, hydrogen peroxide concentration, type and concentration of organic solvent as well as catalyst activity. Typically, however, the amount of catalyst will be from 0.001 to 10 grams per mole of olefin. The concentration of titanium in the total epoxidation reaction mixture will generally be from about 10 to 10,000 ppm.

The catalyst may be utilized in powder, pellet, microspheric, monolithic, extruded, or any other suitable physical form. The use of a binder (co-gel) or support in combination with the titanium-containing molecular sieve may be advantageous. Supported or bound catalysts may be prepared by the methods known in the art to be effective for zeolite catalysts in general.

Illustrative binders and supports (which preferably are non-acidic in character) include silica, alumina, silica-alumina, silica-titania, silica-thoria, silica-magnesia, silica-zironia, silica-beryllia, and ternary compositions of silica with other refractory oxides. Also useful are clays such as montmorillonites, koalins, bentonites, halloysites, dickites, nacrites, and anaxites. The proportion of titanium-containing molecular sieve to binder or support may range from 99:1 to 1:99, but preferably is from 5:95 to 80:20. The catalyst may also be impregnated or admixed with a noble metal such as Pt, Pd, or the like.

The olefin substrate epoxidized in the process of this invention may be any organic compound having at least one ethylenically unsaturated functional group (i.e., a carbon-carbon double bond) and may be a cyclic, branched or straight chain olefin. The olefin may contain aryl groups (e.g., phenyl, naphthyl). Preferably, the olefin is aliphatic in character and contains from 2 to 30 carbon atoms (i.e., a $C_2$–$C_{30}$ olefin). The use of light (low-boiling) $C_2$ to $C_{10}$ mono-olefins is especially advantageous. More than one carbon-carbon double bond may be present in the olefin; dienes, trienes, and other polyunsaturated substrates thus may be used. The double bond may be in a terminal or internal position in the olefin or may alternatively form part of a cyclic structure (as in cyclohexane, for example). Other examples of suitable substrates include unsaturated fatty acids or fatty acid derivatives such as esters or glycerides and oligomeric or polymeric unsaturated compounds such as polybutadiene. Benzylic and styrenic olefins may also be epoxidized, although the epoxides of certain styrenic olefins such as styrene may further react or isomerize under the conditions utilized in the present invention to form aldehydes and the like.

The olefin may contain substituents other than hydrocarbon substituents such as halide, carboxylic acid, ether, hydroxy, thiol, nitro, cyano, ketone, acyl, ester, anhydride, amino, and the like.

Exemplary olefins suitable for use in the process of this invention include ethylene, propylene, the butenes (e.g., 1,2-butene, 2,3-butene, isobutylene), butadiene, the pentenes, isoprene, 1-hexene, 3-hexene, 1-heptene, 1-octene, diisobutylene, 1-nonene, 1-tetradecene, pentamyrcene, camphene, 1-undecene, 1-dodecene, 1-tridecene, 1-tetradecene, 1-pentadecene, 1-hexadecene, 1-heptadecene, 1-octadecene, 1-nonadecene, 1-eicosene, the trimers and tetramers of propylene, styrene (and other vinyl aromatic substrates), polybutadiene, polyisoprene, cyclopentene, cyclohexene, cycloheptene, cyclooctene, cyclooctadiene, cyclododecene, cyclododecatriene, dicyclopentadiene, methylenecyclopropane, methylenecyclopentane, methylenecyclohexane, vinyl cyclohexane, vinyl cyclohexene, methallyl ketone, allyl chloride, allyl bromide, acrylic acid, methacrylic acid, crotonic acid, vinyl acetic acid, crotyl chloride, methallyl chloride, the dichlorobutenes, allyl alcohol, allyl carbonate, allyl acetate, alkyl acrylates and methacrylates, diallyl maleate, dially phthalate, unsaturated triglycerides such as soybean oil, and unsaturated fatty acids, such as oleic acid, linolenic acid, linoleic acid, erucic acid, palmitoleic acid, and ricinoleic acid and their esters (including mono-, di-, and triglyceride esters) and the like.

Mixtures of olefins may be epoxidized and the resulting mixtures of epoxides either employed in mixed form or separated into the different component epoxides.

The process of this invention is especially useful for the epoxidation of $C_2$–$C_{30}$ olefins having the general structure

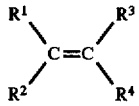

wherein $R^1$, $R^2$, $R^3$, and $R^4$ are the same or different and are selected from the group consisting of hydrogen and $C_1$–$C_{20}$ alkyl.

The oxidizing agent employed in the process of this invention is a hydrogen peroxide source such as hydrogen peroxide ($H_2O_2$) or a hydrogen peroxide precursor (i.e., a compound which under the epoxidation reaction conditions is capable of generating or liberating hydrogen peroxide).

The amount of hydrogen peroxide relative to the amount of olefin is not critical, but most suitably the molar ratio of hydrogen peroxide:olefin is from 100:1 to 1:100 when the olefin contains one ethylenically unsaturated group. The molar ratio of ethylenically unsaturated groups in the olefin substrate to hydrogen peroxide is more preferably in the range of from 1:10 to 10:1. One equivalent of hydrogen peroxide is theoretically required to oxidize one equivalent of a mono-unsaturated olefin substrate, but it may be desirable to employ an excess of one reactant to optimize selectivity to the epoxide. In particular, the use of a small to moderate excess (e.g., 5 to 50%) of olefin relative to hydrogen peroxide may be advantageous for certain substrates.

Although the hydrogen peroxide to be utilized as the oxidizing agent may be derived from any suitable source, a distinct practical advantage of the process of this invention is that the hydrogen peroxide may be obtained by contacting a secondary alcohol such as alpha-methyl benzyl alcohol, isopropyl alcohol, 2-butanol, or cyclohexanol with molecular oxygen under conditions effective to form an oxidant mixture comprised of secondary alcohol and hydrogen peroxide (and/or hydrogen peroxide precursors). Typically, such an oxidant mixture will also contain a ketone such as acetophenone, acetone, or cyclohexanone corresponding to the secondary alcohol (i.e., having the same carbon skeleton), minor amounts of water, and varying amounts of other active oxygen species such as organic hydroperoxides. Molecular oxygen oxidation of anthrahydroquinone, alkyl-substituted anthrahydroquinones, or water-soluble anthrahydroquinone species may also be employed to generate the hydrogen peroxide oxidant. The hydrogen peroxide may be generated in situ immediately prior to or simultaneous with epoxidation, as described, for example, in European Pat. Publication No. 526,945, Japanese Kokai No. 4-352771, Ferrini et al., "Catalytic Oxidation of Alkanes Using Titanium Silicate in the Presence of In-Situ Generated Hydrogen Peroxide", DGMK Conference on Selective Oxidations in Petrochemistry, Sept. 16–18, 1992, pp. 205–213, and European Pat. Pub. No. 469,662.

If desired, a solvent may additionally be present during the epoxidation process of this invention in order to dissolve the reactants other than the titanium-containing molecular sieve catalyst, to provide better temperature control, or to favorably influence the epoxidation rates and selectivities. The solvent, if present, may comprise from 1 to 99 weight percent of the total epoxidation reaction mixture and is preferably selected such that it is a liquid at the epoxidation reaction temperature. Organic compounds having boiling points at atmospheric pressure of from about 25° C. to 300° C. are generally preferred for use. Excess olefin may serve as a solvent or diluent. Illustrative examples of other suitable solvents include, but are not limited to, ketones (e.g., acetone, methyl ethyl ketone, acetophenone), ethers (e.g., tetrahydrofuran, butyl ether), nitriles (e.g., acetonitrile), aliphatic and aromatic hydrocarbons, halogenated hydrocarbons, and alcohols (e.g., methanol, ethanol, isopropyl alcohol, t-butyl alcohol, alpha-methyl benzyl alcohol, cyclohexanol). An important practical advantage of the present invention is that it may readily be practiced using bulkier alcohol solvents such as alpha-methyl benzyl alcohol, whereas poor results are obtained with such solvents when other titanium-containing molecular sieves such as TS-1 are utilized as catalyst. This flexibility minimizes the problems which might otherwise be encountered when trying to separate the epoxide product from the epoxidation reaction mixture. Quantitative removal of methanol, for example, from a relatively light epoxide such as propylene oxide is difficult due to the similarity in their boiling points. More than one type of solvent may be utilized. Water may also be employed as a solvent or diluent; surprisingly, the process of the invention proceeds with minimal hydrolysis even when a significant quantity of water is present in the epoxidation reaction mixture. Biphasic as well as monophasic reaction systems thus are possible using the present invention.

The reaction temperature is not critical, but should be sufficient to accomplish substantial conversion of the olefin to epoxide within a reasonably short period of time. It is generally advantageous to carry out the reaction to achieve as high a hydrogen peroxide conversion as possible, preferably at least 50%, more preferably at least 90% most preferably at least 95%, consistent with reasonable selectivities. The optimum reaction temperature will be influenced by catalyst activity, olefin reactivity, reactant concentrations, and type of solvent employed, among other factors, but typically will be in a range of from about 0° C. to 150° C. (more preferably, from about 25° C. to 120° C.). Reaction or residence times of from about 1 minute to 48 hours (more desirably, from about 10 minutes to 8 hours) will typically be appropriate, depending upon the above-identified variables. Although sub-atmospheric pressures can be employed, the reaction is preferably (especially when the boiling point of the olefin is below the epoxidation reaction temperature) performed at atmospheric pressure or at elevated pressure (typically, between 1 and 100 atmospheres). Generally, it will be desirable to pressurize the epoxidation vessel sufficiently maintain the reaction components as a liquid phase mixture. Most (i.e., over 50%) of the olefin should preferably be present in the liquid phase.

The process of this invention may be carried out in a batch, continuous, or semi-continuous manner using any appropriate type of reaction vessel or apparatus such as a fixed bed, transport bed, fluidized bed, stirred slurry, or CSTR reactor in a monophase or biphase system. Known methods for conducting metal-catalyzed epoxidations of olefins using hydrogen peroxide will generally also be suitable for use in this process. Thus, the reactants may be combined all at once or sequentially. For example, the hydrogen peroxide or hydrogen peroxide precursor may be added incrementally to the reaction zone. The hydrogen peroxide could also be generated in situ within the same reactor zone where epoxidation is taking place. Once the epoxidation has been carried out to the desired degree of conversion, the epoxide product may be separated and recovered from the reaction mixture using any appropriate technique such as fractional distillation, extractive distillation, liquid-liquid extraction, crystallization, or the like. After separating from the epoxidation reaction mixture by any suitable method such as filtration, the recovered catalyst may be economically re-used in subsequent epoxidations. Where the catalyst is deployed in the form of a fixed bed, the epoxidation product withdrawn as a stream from the epoxidation zone will be essentially catalyst free with the catalyst being retained within the epoxidation zone. In certain embodiments of the instant process where the epoxide is being produced on a continuous basis, it may be desirable to periodically or constantly regenerate all or a portion of the used titanium-containing molecular sieve catalyst in order to maintain optimum activity and selectivity. Suitable regeneration techniques include, for example, treating the catalyst with solvent, calcining the catalyst, and/or contacting the catalyst with an ammonium, alkali metal or alkaline earth compound. Any unreacted olefin or hydrogen peroxide may be similarly separated and recycled. Alternatively, the unreacted hydrogen peroxide (especially if present at concentrations too low to permit economic recovery) could be thermally or chemically decomposed into non-peroxy species such as water and oxygen, for example. In certain embodiments of the process where the hydrogen peroxide is generated by molecular oxygen oxidation of a secondary alcohol, the crude epoxidation reaction mixture will also contain a secondary alcohol and a ketone corresponding to the secondary alcohol. After separation of the epoxide from the secondary alcohol and the corresponding ketone, the ketone may be converted back to secondary alcohol by hydrogenation. For example, the ketone may be reacted with hydrogen in the presence of a transition metal hydrogenation catalyst such as a Raney nickel, copper chromite, ruthenium, or supported palladium catalyst. Hydrogenation reactions of this type are well known to those skilled in the art. The secondary alcohol may also be dehydrated using known methods to yield valuable alkenyl products such as styrene.

The titanium-containing molecular sieve described herein, in addition to being a useful epoxidation catalyst, also has utility as an ion exchanger, a shape-selective separation medium, or a catalyst for other hydrocarbon conversion processes, including, for example: cracking, selectoforming, hydrogenation, dehydrogenation, oligomerization, alkylation, isomerization, dehydration, hydroxylation of olefins or aromatics, alkane oxidation, reforming, disproportionation, methanation, and the like. The molecular sieve of this invention is particularly useful for catalyzing the same reactions wherein titanium silicalites (also referred to as titanium silicates) have heretofore been employed. Illustrative applications of this type are as follows:

a) A process for the manufacture of a ketone oxime which comprises reacting a ketone such as cyclohexanone with ammonia and hydrogen peroxide in the liquid phase at a temperature of from 25° C. to 150° C. in the presence of a catalytically effective amount of the titanium-containing molecular sieve. Reactions of this type are well known in the art and suitable conditions for carrying out such a synthetic transformation in the presence of a titanium silicalite catalyst are described, for example, in U.S. Pat. No. 4,745,221, Roffia et al., "Cyclohexanone Ammoximation: A Breakthrough in the 6-Caprolactam Production Process", in *New Developments in Selective Oxidation*, Centi et al, eds., pp. 43–52 (1990), Roffia et al., "A New Process for Cyclohexanonoxime", *La Chimica & L'Industria* 72, pp. 598–603 (1990), U.S. Pat. No. 4,894,478, U.S. Pat. No. 5,041,652, U.S. Pat. No. 4,794,198, Reddy et al., "Ammoximation of Cyclohexanone Over a Titanium Silicate Molecular Sieve", *J. Mol. Cat.* 69, 383–392 (1991), European Pat. Pub. No. 496,385, European Pat. Pub. No. 384,390, and U.S. Pat. No. 4,968,842, (the teachings of the foregoing publications are incorporated herein by reference in their entirety).

(b) A process for oxidizing a paraffinic compound (i.e., a saturated hydrocarbon) comprising reacting the paraffinic compound at a temperature of from 25° C. to 200° C. with hydrogen peroxide in the presence of a catalytically effective amount of the titanium-containing molecular sieve. Reactions of this type are well known in the art and suitable conditions for carrying out such a synthetic transformation in the presence of a titanium silicalite are described, for example, in Huybrechts et al., *Nature* 345,240 (1990), Clerici, *Appl. Catal.* 68, 249 (1991), and Tatsumi et al., *J. Chem. Soc. Chem. Commun.* 476 (1990), Huybrechts et al., *Catalysis Letters* 8, 237–244 (1991), the teachings of which are incorporated herein by reference in their entirety.

(c) A process for hydroxylating an aromatic hydrocarbon (e.g., phenol) comprising reacting the aromatic compound at a temperature of from 50° to 150° C. with hydrogen peroxide in the presence of a catalytically effective amount of the titanium-containing molecular sieve to form a phenolic compound (e.g., cresol) Reactions of this type are well known in the art and suitable conditions for carrying out such a synthetic transformation in the presence of a titanium silicalite catalyst are described, for example, in U.S. Pat. No. 4,396,783, Romano et al., "Selective Oxidation with Ti-silicalite", *La Chimica L'Industria* 72, 610–616 (1990), Reddy et al., *Applied Catalysis* 58, L1–L4 (1990), (d) A process for isomerizing an aryl-substituted epoxide to the corresponding beta-phenyl aldehyde comprising contacting the aryl-substituted epoxide with a catalytically effective amount of the titanium-containing molecular sieve at a temperature of from 25° C. to 150° C. See, for example, U.S. Pat. No. 4,495,371 (incorporated herein by reference in its entirety).

(e) A process for oxidizing a vinyl benzene compound to the corresponding beta-phenyl aldehyde comprising reacting the vinyl benzene compound with hydrogen peroxide at a temperature of from 20° C. to 1500° C. in the presence of the titanium-containing molecular sieve. See, for example, U.S. Pat. No. 4,609,765 (incorporated herein by reference in its entirety).

(f) A process for synthesizing an N,N-dialkyl hydroxylamine comprising reacting the corresponding secondary dialkyl amine with hydrogen peroxide in the presence of the titanium-containing molecular sieve. See, for example, U.S. Pat. No. 4,918,194 (incorporated herein by reference in its entirety).

(g) A process for oxidizing an aliphatic alcohol comprising reacting the aliphatic alcohol with hydrogen peroxide in the presence of the titanium-containing molecular sieve at a temperature of from 25° C. to 150° C. to form the corresponding ketone or aldehyde of said aliphatic alcohol. See, for example, U.S. Pat. No. 4,480,135 (incorporated herein by reference in its entirety).

(h) A process for synthesizing a glycol monoalkyl ether comprising reacting an olefin, an aliphatic alcohol, and hydrogen peroxide in the presence of the titanium-containing molecular sieve at a temperature of from 25° C. to 150° C. See, for example, U.S. Pat. No. 4,476,327 (incorporated herein by reference in its entirety).

From the foregoing description, one skilled in the art can readily ascertain the essential characteristics of this invention, and, without departing from the spirit and scope thereof, can make various changes and modifications of the invention to adapt it to various usages, conditions, and embodiments.

The following examples further illustrate the process of this invention, but are not limitative of the invention in any manner whatsoever.

EXAMPLE 1

This example demonstrates the preparation of a titanium-containing molecular sieve in accordance with the present invention and its utility an olefin epoxidation catalyst.

Calcined zeolite beta (5 g; Conteka 41-89-001) having a $SiO_2:Al_2O_3$ ratio of 24 is added to 500 ml of 13N nitric acid. The resulting suspension is heated at 80° C. for four hours with stirring. The suspended solids are recovered by filtration and retreated twice in the same manner with fresh portions of 13N nitric acid. After recovering by filtration, the solids are washed well with deionized water, and dried at 95° C. overnight to provide a dealuminated zeolite beta having a Si/Al molar ratio of 940.

The dealuminated zeolite beta is added to a fitted quartz tube. The tube is loaded vertically in a furnace and a slow (100 cc/min) nitrogen flow initiated. The sample is heated at 400° C., then heated at 600° C. and the nitrogen flow increased to 300 cc/min. Once the temperature has stabilized at 600° C., the sample is treated with titanium tetrachloride for eight hours by sparging the nitrogen feed through a warmed (40° C.) $TiCl_4$ solution. After this time, $TiCl_4$ treatment is discontinued and nitrogen flow through the sample continued at 600° C. for an additional hour. The sample is cooled to room temperature overnight with continuous nitrogen flow. The cooled sample is treated with a 1M aqueous solution of ammonium nitrate at 80° C. for four hours. The sample is recovered by filtration, washed well with water, dried at 95° C. and then calcined at 550° C. for 6 hours to yield a titanium-containing molecular sieve having a very low level of aluminum. Raman spectroscopy and $^{29}Si$ and $^{27}Al$ MAS NMR also confirmed that near complete dealumination takes place and that titanium is inserted into the framework of the zeolite. The x-ray powder diffraction pattern of the titanium-containing molecular sieve is shown in FIG. 1 and summarized in Table II. From $^{27}Al$ MAS NMR, it is estimated that less than 100 ppm aluminum is present.

The titanium-continuing molecular sieve thus obtained is evaluated as a catalyst for the hydrogen peroxide epoxidation of 1-hexene using the following condition: 60° C., 12.2 g methanol (solvent), 16.5 mmol 1-hexene, 4.5 mmol hydrogen peroxide, 0.10 g catalyst.

The results of this evaluation are shown in Table I. Example 1-A shows that good epoxide selectivity can be achieved without modification of the catalyst with Group IA or Group IIA cations, due (it is believed) to the extremely low aluminum content of the catalyst. The activity of the catalyst was quite high, with over 90% conversion of hydrogen peroxide being attained in just one hour. When the catalyst was washed with 0.5% sodium acetate (Example 1-B), a somewhat lower initial rate of hydrogen peroxide reaction was observed together with improved selectivity. Example 1-C demonstrates that the titanium-containing molecular sieve which has been treated with sodium acetate also performs quite satisfactorily if alpha-methyl benzyl alcohol rather than methanol is used as a solvent for epoxidation. In contrast, titanium silicalite having a TS-1 structure exhibited little activity in an alpha-methyl benzyl alcohol medium (Example 1-D).

TABLE I

| Example | Solvent | Catalyst Treatment | Time, hr | H$_2$O$_2$ Conversion % | Epoxide Selectivity, %[a] | Glycol Ether Selectivity, %,[a] | Hexene Conversion, % | Epoxide/Glycol Ether Ratio |
|---|---|---|---|---|---|---|---|---|
| 1-A | methanol | none | 1 | 93 | 58 | 1.7 | 19 | 3 |
|  |  |  | 6 | 96 | 52 | (+17% other) 3 (+39% Other) | 31 | 1 |
| 1-B | methanol | 0.5% NaOAc | 1 | 68 | 75 | 5 | 16 | 15 |
|  |  |  | 6 | 97 | 63 | 19 | 23 | 4 |
| 1-C | alpha methyl benzyl alcohol | 0.5% NaOAc | 1 | 98 | 68 | <2 | 18.4 | >50 |
| 1-D[c] | alpha methyl benzyl alcohol | —[b] | 1 | no reaction | — | — | — | — |

[a]based on hydrogen peroxide
[b]TS-1 catalyst (U.S. Pat. No. 4,410,501)
[c]comparative example

TABLE II

| d(angstroms) | Relative Intensity |
|---|---|
| 11.50 | vs |
| 6.57 | mw |
| 6.05 | mw |
| 4.13 | w |
| 3.95 | s |
| 3.51 | mw |
| 3.28 | mw |
| 3.24 | mw |
| 3.19 | w |
| 3.02 | w |
| 2.68 | w |
| 2.48 | w |
| 2.08 | w |
| 1.69 | w | d = interplanar distance
vs = very strong
s = strong
mw = medium weak
w = weak

We claim:

1. A crystalline titanium-containing molecular sieve characterized by a framework structure isomorphous to zeolite beta and comprised of Si and Ti having a Si:Al molar ratio of at least 750, corresponding to the general formula SiO$_2$:yTiO$_2$ wherein y is from 0.01 to 0.25.

2. The molecular sieve of claim 1 wherein the Si:Al molar ratio is at least 1000.

3. The molecular sieve of claim 1 having a characteristic x-ray pattern as set fourth in FIG. 1.

4. The molecular sieve of claim 1 wherein y is from 0.03 to 0.20.

5. The molecular sieve of claim 1 having a titanium content of from 1 to 10 weight percent.

6. A crystalline titanium-containing molecular sieve characterized by a framework structure isomorphous to zeolite beta and comprised of Si and Ti having a Si:Al molar ratio of at least 1000, corresponding to the general formula SiO$_2$:yTiO$_2$ wherein y is from 0.03 to 0.20 and having a crystallinity greater than 75%.

* * * * *

UNITED STATES PATENT AND TRADEMARK OFFICE
CERTIFICATE OF CORRECTION

PATENT NO. : 5,695,736
DATED : Dec. 9, 1997
INVENTOR(S) : Saxton et al.

It is certified that error appears in the above-identified patent and that said Letters Patent is hereby corrected as shown below:

On the title page item [54], delete "TIATANIUM" and
insert therefor --TITANIUM-- delete "ZELITE" and
insert therefor --ZEOLITE"

Column 12, line 31: delete "fourth" and
insert therefor --forth--

Signed and Sealed this

Third Day of March, 1998

Attest:

BRUCE LEHMAN

Attesting Officer          Commissioner of Patents and Trademarks